(12) United States Patent
Chung et al.

(10) Patent No.: US 11,187,646 B2
(45) Date of Patent: Nov. 30, 2021

(54) DIAGNOSTIC KIT AND CONTROL METHOD THEREOF

(71) Applicant: ABSOLOGY CO., LTD., Anyang-si (KR)

(72) Inventors: Seok Chung, Seoul (KR); Joon Seok Seo, Yongin-si (KR); Jae Un Jeong, Hwaseong-si (KR); Han Sang Jo, Gwacheon-si (KR)

(73) Assignee: ABSOLOGY CO., LTD., Anyang-si (KR)

( * ) Notice: Subject to any disclaimer, the term of this patent is extended or adjusted under 35 U.S.C. 154(b) by 288 days.

(21) Appl. No.: 16/464,289

(22) PCT Filed: Nov. 19, 2018

(86) PCT No.: PCT/KR2018/014159
§ 371 (c)(1),
(2) Date: May 27, 2019

(87) PCT Pub. No.: WO2019/132249
PCT Pub. Date: Jul. 4, 2019

(65) Prior Publication Data
US 2020/0292442 A1 Sep. 17, 2020

(30) Foreign Application Priority Data
Dec. 29, 2017 (KR) .......................... 10-2017-0183699

(51) Int. Cl.
*G01N 21/01* (2006.01)
*G01N 1/28* (2006.01)

(52) U.S. Cl.
CPC ............... *G01N 21/01* (2013.01); *G01N 1/28* (2013.01); *G01N 2021/015* (2013.01)

(58) Field of Classification Search
CPC .... G01N 21/05; G01N 21/01; G01N 21/0346; G01N 15/1404; G01N 2021/558; G01N 2021/7763; G01N 2021/058; B01L 9/527
(Continued)

(56) References Cited

U.S. PATENT DOCUMENTS

| 2002/0064480 A1 | 5/2002 | Shartle |
| 2010/0144020 A1 | 6/2010 | Kim et al. |

(Continued)

FOREIGN PATENT DOCUMENTS

| KR | 10-2000-0011826 A | 2/2000 |
| KR | 10-2010-0065538 A | 6/2010 |

(Continued)

OTHER PUBLICATIONS

International Search Report for PCT/KR2018/014159 dated Feb. 25, 2019 from Korean Intellectual Property Office.

*Primary Examiner* — Hoa Q Pham
(74) *Attorney, Agent, or Firm* — Revolution IP, PLLC (57) ABSTRACT

A diagnostic kit includes: a diagnostic chip formed with a flow channel through which a diagnostic sample moves; a diagnostic sample movement regulation unit opening/closing one end of the flow channel to regulate movement of the diagnostic sample; an optical information detection unit detecting optical information on the diagnostic sample; and a controller controlling operation of the diagnostic sample movement regulation unit and the optical information detection unit, wherein the optical information detection unit includes: a light source illuminating the diagnostic sample; and a sensor sensing the optical information from the diagnostic sample, the diagnostic sample movement regulation unit is operatively associated with the optical information detection unit, and the diagnostic chip and the optical information detection unit are moved relative to each other (Continued)

upon operation of the diagnostic sample movement regulation unit.

20 Claims, 8 Drawing Sheets

(58) Field of Classification Search
USPC ..... 356/246, 432–440, 36; 435/287.2, 287.1, 435/288.3, 288.5; 422/68.1, 82.05, 401, 422/502, 504, 63, 430, 82, 9, 82.09
See application file for complete search history.

(56) References Cited

U.S. PATENT DOCUMENTS

| | | | |
|---|---|---|---|
| 2013/0027695 A1* | 1/2013 | Salsman | F04B 19/006 356/246 |
| 2013/0306160 A1 | 11/2013 | Chung et al. | |
| 2015/0036131 A1* | 2/2015 | Salsman | G02B 21/365 356/244 |
| 2015/0037786 A1* | 2/2015 | Salsman | G02B 21/16 435/5 |
| 2016/0246044 A1* | 8/2016 | Salsman | G02B 21/0008 |

FOREIGN PATENT DOCUMENTS

| | | |
|---|---|---|
| KR | 10-2013-0128937 A | 11/2013 |
| KR | 10-2015-0029290 A | 3/2015 |
| KR | 10-2015-0031007 A | 3/2015 |
| KR | 10-1897131 B1 | 9/2018 |
| WO | 2009/139311 A1 | 11/2009 |

\* cited by examiner

DIAGNOSTIC KIT AND CONTROL METHOD THEREOF

TECHNICAL FIELD

The present invention relates to a diagnostic kit and a method of controlling the same. More particularly, the present invention relates to a diagnostic kit which regulates movement of a diagnostic sample moving through a flow channel of a diagnostic chip through a diagnostic sample movement regulation unit while moving the diagnostic chip by controlling a diagnostic chip movement regulation unit moving the diagnostic chip upon operation of the diagnostic sample movement regulation unit, thereby allowing more accurate diagnosis of disease, and a method of controlling the same.

BACKGROUND ART

With increase in life expectancy of modern people and hence increase in the variety of accompanying diseases, various diagnostic devices and systems have been developed for prevention and diagnosis of diseases.

Thereamong, a diagnostic kit is used to examine the presence of a single or multiple substances in a liquid sample, for example, a urine or blood sample. Specifically, today's diagnostics industries are being integrated into point-of-care testing (POCT). POCT refers to testing performed outside a central laboratory using a device that can be handled by any non-expert user. Currently, diagnostic areas are extended to the site of patient care and individual areas without being limited to hospitals.

For example, POCT may be applied when there is a need to draw a small amount of blood to examine the presence of an adequate amount of antibiotics in the blood for a patient taking large doses of antibiotics in a hospital to resist infection, or when there is a need to promptly examine the kinds of drugs ingested into the body to secure proper treatment for an overdose patient with impaired cognitive function or an infant unable to communicate.

Particularly, rapid diagnostic tests, represented by immunochromatographic assay, are used in the healthcare industry to identify diseases or to determine changes of diseases. In various fields such as food and biological processing and environmental management, the rapid diagnostic tests are being developed as a simple method to qualitatively and quantitatively examine a trace amount of analyte. Also, in the healthcare industry, use thereof is being extended to diagnosis of pregnancy, ovulation, infectious diseases, drug abuse, acute myocardial infarction, and cancer.

A typical way of diagnosing diseases using a diagnostic kit is pretreating a diagnostic sample, illuminating the diagnostic sample, and diagnosing diseases based on optical information emitted from the diagnostic sample. However, this method has a problem in that the speed at which the diagnostic sample travels in the diagnostic kit is so fast that there is not enough time to pretreat the diagnostic sample and the optical information from the diagnostic sample is thus inaccurate, causing difficulty in determination of diseases.

In addition, since detection of the optical information is conducted during traveling of the diagnostic sample, only one measurement per area is possible, causing reduction in detection accuracy.

DISCLOSURE

Technical Problem

It is an aspect of the present invention to provide a diagnostic kit which regulates movement of a diagnostic sample moving through a flow channel of a diagnostic chip through a diagnostic sample movement regulation unit while moving the diagnostic chip by controlling a diagnostic chip movement regulation unit moving the diagnostic chip upon operation of the diagnostic sample movement regulation unit, thereby allowing more accurate diagnosis of disease, and a method of controlling the same.

Technical Solution

In accordance one aspect of the present invention, a diagnostic kit includes: a diagnostic chip formed with a flow channel through which a diagnostic sample moves; a diagnostic sample movement regulation unit opening/closing one end of the flow channel to regulate movement of the diagnostic sample; an optical information detection unit detecting optical information on the diagnostic sample; and a controller controlling operation of the diagnostic sample movement regulation unit and the optical information detection unit, wherein the optical information detection unit includes: a light source illuminating the diagnostic sample; and a sensor sensing the optical information emitted from the diagnostic sample, the diagnostic sample movement regulation unit is operatively associated with the optical information detection unit, and the diagnostic chip and the optical information detection unit are moved relative to each other upon operation of the diagnostic sample movement regulation unit, whereby the optical information detection unit detects the optical information on the diagnostic sample moving through the flow channel.

Upon operation of the diagnostic sample movement regulation unit, the optical information detection unit may be moved by the controller to be moved relative to the diagnostic chip.

The diagnostic kit may further include a diagnostic chip movement regulation unit moving the diagnostic chip, wherein relative movement between the diagnostic chip and the optical information detection unit may be achieved through operative association between the diagnostic chip movement regulation unit and the diagnostic sample movement regulation unit.

Upon operation of the diagnostic sample movement regulation unit, the diagnostic chip movement regulation unit may be operated by the controller to move the diagnostic chip, thereby allowing relative movement between the diagnostic chip and the optical information detection unit.

Upon operation of the diagnostic sample movement regulation unit, the optical information detection unit and the diagnostic chip movement regulation unit may be simultaneously operated by the controller to control movement of the diagnostic chip and movement of the optical information detection unit, thereby allowing relative movement between the diagnostic chip and the optical information detection unit.

The diagnostic chip may include: a diagnostic chip housing including an upper plate and a lower plate and formed therein with the flow channel; a diagnostic sample input opening formed on the upper plate and connected to the other end of the flow channel to allow the diagnostic sample to be introduced therethrough; a pretreatment unit disposed in a first region of the flow channel and provided with a material for pretreatment of the diagnostic sample moved from the diagnostic sample input opening; a test unit disposed in a second region of the flow channel and provided with a material for testing of the diagnostic sample moved from the first region; and a reference unit disposed in a third region of the flow channel and provided with a reference material of the diagnostic sample moved from the second region.

Sensing of the optical information on the diagnostic sample may be performed in such a way that the diagnostic sample movement regulation unit opens the one end of the flow channel to move the diagnostic sample such that at least one of the diagnostic chip movement regulation unit and the optical information detection unit is operated to move at least one of the diagnostic chip and the optical information detection unit, while the light source and the sensor sense the optical information on the diagnostic sample by illuminating the diagnostic sample, or in such a way that the diagnostic sample movement regulation unit opens/closes the one end of the flow channel at a predetermined time interval such that at least one of the diagnostic chip movement regulation unit and the optical information detection unit is operated to move/stop at least one of the diagnostic chip and the optical information detection unit depending on position of the diagnostic sample, and the light source and the sensor sense the optical information on the diagnostic sample by illuminating the diagnostic sample when the diagnostic sample and the diagnostic chip are in a stationary state.

The controller may regulate movement of the diagnostic sample by controlling operation of the diagnostic sample movement regulation unit according to a predetermined timing scheme.

Data on a moving speed of the diagnostic sample may be prestored in the controller and the controller may regulate movement of the diagnostic sample and movement of the diagnostic chip by controlling operation of the diagnostic sample movement regulation unit and operation of at least one of the diagnostic chip movement regulation unit and the optical information detection unit according to a predetermined timing scheme based on the data on the moving speed of the diagnostic sample.

The controller may regulate movement of the diagnostic sample and movement of the diagnostic chip by controlling operation of the diagnostic sample movement regulation unit and operation of at least one of the diagnostic chip movement regulation unit and the optical information detection unit based on the optical information on the diagnostic sample acquired by the sensor.

The diagnostic kit may further include an image viewer unit showing a moving image of the diagnostic sample, wherein the controller may regulate movement of the diagnostic sample and the diagnostic chip by controlling operation of the diagnostic sample movement regulation unit and operation of at least one of the diagnostic chip movement regulation unit and the optical information detection unit based on movement of the diagnostic sample ascertained through the image viewer unit.

In accordance with another aspect of the present invention, a method of controlling a diagnostic kit includes: a diagnostic sample input step in which a diagnostic sample is introduced into a flow channel formed in a diagnostic chip through a diagnostic sample input opening; a diagnostic sample moving step in which the diagnostic sample is moved along the flow channel; a detection position adjustment step in which, upon movement of the diagnostic sample, the diagnostic chip and an optical information detection unit detecting optical information on the diagnostic sample are moved relative to each other to adjust a position for detecting the optical information on the diagnostic sample; and an optical information detection step in which the optical information detection unit detects the optical information on the diagnostic sample, the optical information detection step including: an illumination step in which a light source illuminates the diagnostic sample; and an optical information sensing step in which a sensor senses the optical information from the diagnostic sample, wherein the diagnostic sample moving step and the detection position adjustment step are conducted by a controller, and movement of the diagnostic sample in the diagnostic sample moving step is regulated by a diagnostic sample movement regulation unit opening/closing one end of the flow channel, and, in the detection position adjustment step, the optical information detection unit is operatively associated with the diagnostic sample movement regulation unit to be controlled by operation of the diagnostic sample movement regulation unit.

In the detection position adjustment step, upon operation of the diagnostic sample movement regulation unit, the optical information detection unit may be moved by the controller to be moved relative to the diagnostic chip.

The detection position adjustment step may include a diagnostic chip moving step in which the diagnostic chip is moved by a diagnostic chip movement regulation unit and the relative movement between the diagnostic chip and the optical information detection unit in the detection position adjustment step may be achieved through operative association between the diagnostic chip movement regulation unit and the diagnostic sample movement regulation unit.

In the detection position adjustment step, the diagnostic chip movement regulation unit may be operated by the controller upon operation of the diagnostic sample movement regulation unit to move the diagnostic chip, thereby allowing relative movement between the diagnostic chip and the optical information detection unit.

In the detection position adjustment step, the optical information detection unit and the diagnostic chip movement regulation unit may be simultaneously operated by the controller upon operation of the diagnostic sample movement regulation unit so as to control movement of the diagnostic chip and the optical information detection unit, thereby allowing relative movement between the diagnostic chip and the optical information detection unit.

The diagnostic sample moving step may include: a pretreatment step in which the diagnostic sample moved from the diagnostic sample input opening is pretreated in a first region; a test step in which the diagnostic sample moved from the first region is tested in a second region; and a reference level identification step in which a reference level of the diagnostic sample moved from the second region is identified in a third region.

Sensing of the optical information on the diagnostic sample may be performed in such a way that, in the diagnostic sample moving step, the diagnostic sample movement regulation unit opens the one end of the flow channel to move the diagnostic sample such that at least one of the diagnostic chip movement regulation unit and the optical information detection unit is operated to move at least one of the diagnostic chip and the optical information detection unit in the detection position adjustment step, while the light source and the sensor sense the optical information on the diagnostic sample by illuminating the diagnostic sample, or in such a way that, in the diagnostic sample moving step, the diagnostic sample movement regulation unit opens/closes the one end of the flow channel at a predetermined time interval such that at least one of the diagnostic chip movement regulation unit and the optical information detection unit is operated to move/stop at least one of the diagnostic chip and the optical information detection unit depending on position of the diagnostic sample in the detection position adjustment step, and the light source and the sensor sense the optical information on the diagnostic sample by illuminating the diagnostic sample when the diagnostic sample and the diagnostic chip are in a stationary state.

In the diagnostic sample moving step, the controller may regulate movement of the diagnostic sample by controlling operation of the diagnostic sample movement regulation unit according to a predetermined timing scheme.

In the diagnostic sample moving step, the controller may operate the diagnostic sample movement regulation unit based on data on a moving speed of the diagnostic sample, the data being prestored in the controller, and, in the detection position adjustment step, the controller may regulate movement of the diagnostic sample and the diagnostic chip by controlling operation of at least one of the diagnostic chip movement regulation unit and the optical information detection unit according to a predetermined timing scheme.

In the diagnostic sample moving step, the controller may operate the diagnostic sample movement regulation unit based on the optical information on the diagnostic sample acquired by the sensor, and, in the detection position adjustment step, the controller may regulate movement of the diagnostic sample and the diagnostic chip by controlling operation of at least one of the diagnostic chip movement regulation unit and the optical information detection unit.

The diagnostic sample moving step may include an image viewing step in which a moving image of the diagnostic sample moving though the flow channel is viewed through an image viewer unit, wherein the controller may operate the diagnostic sample movement regulation unit based on movement of the diagnostic sample ascertained through the image viewer unit in the diagnostic sample moving step and may regulate movement of the diagnostic sample and the diagnostic chip in the detection position adjustment step by controlling operation of at least one of the diagnostic chip movement regulation unit and the optical information detection unit.

Advantageous Effects

The diagnostic kit according to the present invention provides the following effects:

First, since the diagnostic chip movement regulation unit is operatively associated with the diagnostic sample movement regulation unit to be controlled by operation of the diagnostic sample movement regulation unit, an additional device and process for controlling the diagnostic chip movement regulation unit can be omitted, thereby allowing easier diagnosis of disease.

Second, since the diagnostic sample movement regulation unit can move/stop the diagnostic sample moving through the flow channel by opening/closing the flow channel opening/closing portion at a predetermined time interval, the diagnostic sample can sufficiently react with respective materials in the sample buffer unit, the pretreatment unit, the test unit, and the reference unit depending on the position at which the diagnostic sample is stopped, thereby enabling more accurate diagnosis of disease.

Third, since the diagnostic sample movement regulation unit can move/stop the diagnostic sample moving through the flow channel by opening/closing the flow channel opening/closing portion at a predetermined time interval, when the diagnostic sample is in a stationary state, color information on the diagnostic sample at the same location can be measured several times through the light source and the sensor, thereby allowing more accurate determination of the color information obtained from the diagnostic sample and thus enabling more accurate diagnosis of disease.

BEST MODE

Hereinafter, embodiments of the present invention will be described with reference to the accompanying drawings. It should be noted that like components will be denoted by like reference numerals throughout the specification and the accompanying drawings. In addition, description of details apparent to those skilled in the art will be omitted for clarity.

A diagnostic kit according to one embodiment of the present invention will be described with reference to FIG. 1 to FIG. 6.

Referring to FIG. 1 to FIG. 6, the diagnostic kit according to the present invention includes a main body 500, a diagnostic chip, a diagnostic sample movement regulation unit 200, a diagnostic chip movement regulation unit (not shown), an optical information detection unit, and a controller (not shown), and an image viewer unit 600.

Figure 1:
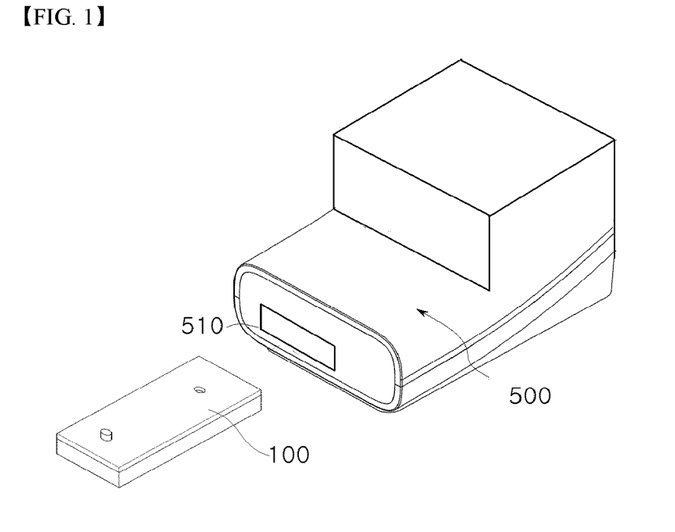
FIG. 1 is a schematic view of a diagnostic kit according to one embodiment of the present invention.
Figure 2:
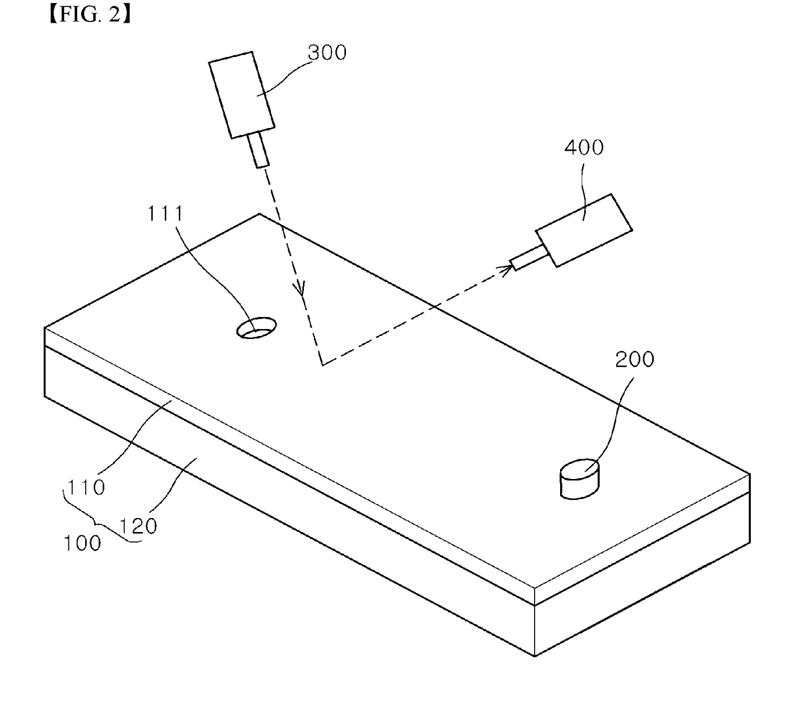
FIG. 2 is a schematic view showing positional relation between a diagnostic chip, a light source, and a sensor of the diagnostic kit of FIG. 1.
Figure 3:
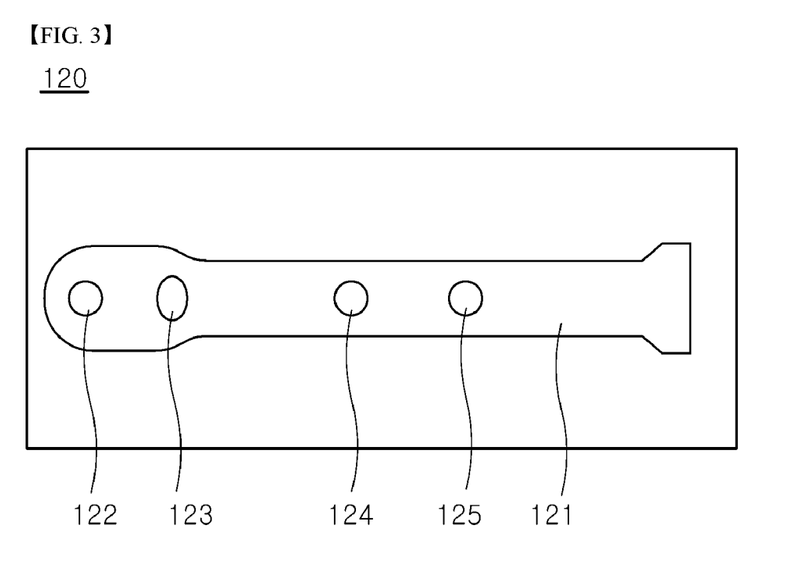
FIG. 3 is a view of a sample buffer unit, a pretreatment unit, a test unit, and a reference unit formed on a flow channel of the diagnostic kit of FIG. 2.
Figure 4:
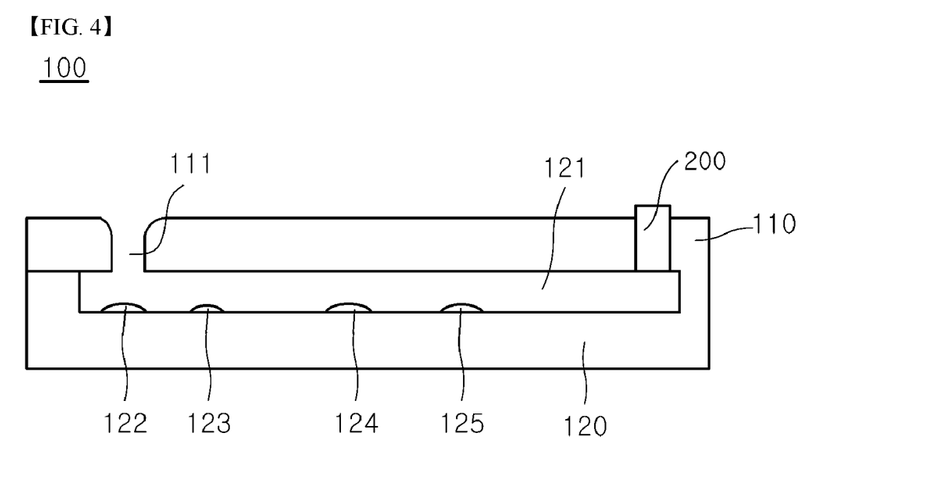
FIG. 4 is a sectional view of the diagnostic kit of FIG. 2.

The diagnostic sample movement regulation unit 200, the diagnostic chip movement regulation unit, the optical information detection unit, the controller, and the image viewer unit 600 are located inside the main body 500. The diagnostic chip is inserted into a diagnostic chip insertion opening 510 formed through the main body 500 and the optical information detection unit 300, 400 described below is located above the diagnostic chip, as shown in FIG. 2. Positional relation between the other components will be described further below.

The diagnostic chip is formed therein with a flow channel 121 allowing a diagnostic sample S to move therethrough and is moved by the diagnostic chip movement regulation unit. Specifically, the diagnostic chip includes a diagnostic chip housing 100, a diagnostic sample input opening 111, a sample buffer unit 122, a pretreatment unit 123, a test unit 124, and a reference unit 125.

The diagnostic chip housing 100 includes an upper plate 110 and a lower plate 120 and is formed therein with the flow channel 121.

The upper plate 110 is coupled to an upper surface of the lower plate 120 and is formed with the diagnostic sample input opening 111 and a flow channel opening/closing portion (not indicated by reference numeral).

The flow channel opening/closing portion is formed at one end of the flow channel 121 to allow the diagnostic sample movement regulation unit 200 described below to be removably coupled thereto, and the diagnostic sample input opening 111 is formed on the upper plate 110 and is connected to the other end of the flow channel 121 to allow the diagnostic sample S to be moved into the flow channel 121 therethrough.

Preferably, the upper plate 110 is formed of a transparent material. In this way, the optical information detection unit can detect optical information from the diagnostic sample S upon illuminating the diagnostic sample S, whereby diagnosis of disease can be smoothly performed without exposing the diagnosis sample S to the outside.

Here, the optical information detected by the optical information detection unit includes quantity of light from the diagnosis sample, such as color development, luminescence intensity, and fluorescence intensity, wavelength of light from the diagnosis sample, and polarization of light from the diagnostic sample. It should be understood that the present invention is not limited thereto and the optical information may include any information that can be detected by illuminating the diagnostic sample passing through the sample buffer unit, the pretreatment unit, the test unit, or the reference unit, described below.

The optical information detection unit includes a light source 300 illuminating the diagnostic sample and a sensor 400 sensing the optical information emitted from the diagnostic sample.

The lower plate 120 is coupled to a lower surface of the upper plate 110 and is formed of a material that does not react with the diagnostic sample S and does not affect the diagnostic sample S. In addition, the lower plate 120 is formed on the upper surface thereof with the flow channel 121 through which the diagnostic sample S moves.

The sample buffer unit 122 is formed in a $0^{th}$ (zeroth) region of the flow channel 121, that is, in a region of the flow channel 121 corresponding to the diagnostic sample input opening 111. The sample buffer unit 122 is provided with a sample buffer material that stabilizes the diagnostic sample S. The sample buffer unit 122 may include a plurality of sample buffer units depending upon the kind of diagnostic sample S and the sample buffer material may be varied depending on the kind of diagnostic sample S and target material.

The pretreatment unit 123 is formed in a first region of the flow channel 121, that is, in a region of the flow channel 121 downstream of the zeroth region in a moving direction of the diagnostic sample S.

The pretreatment unit 123 is provided with a pretreatment material that is used to pretreat the diagnostic sample S introduced through the diagnostic sample input opening 111 and having been buffered in the zeroth region. The pretreatment unit 123 may include a plurality of pretreatment units depending on the kind of diagnostic sample S and the pretreatment material may be varied depending on the kind of diagnostic sample S and target material.

The test unit 124 is formed in a second region of the flow channel 121, that is, in a region of the flow channel 121 downstream of the first region in the moving direction of the diagnostic sample S.

The test unit 124 is provided with a test material that is used to test the diagnostic sample S pretreated in the second region, whereby diagnosis of disease can be conducted based on the optical information from the diagnostic sample S by illuminating the diagnostic sample S passing through the test unit 124.

The test unit 124 may include a plurality of test units depending on the kind of diagnostic sample S and the test material may be varied depending on the kind of diagnostic sample S and target material.

The reference unit 125 is formed in a third region of the flow channel 121, that is, in a region of the flow channel 121 downstream of the second region in the moving direction of the diagnostic sample S.

The reference unit 125 is provided with a reference material that is used to identify a reference level of the diagnostic sample S subjected to a test for diagnosis of disease in the third region, whereby the reference level of the diagnostic sample S can be identified based on the optical information from the diagnostic sample S by illuminating the diagnostic sample S passing through the reference unit 125.

The reference unit 125 may include a plurality of reference units depending on the kind of diagnostic sample S and the reference material may be varied depending on the kind of diagnostic sample S and target material.

The diagnostic chip movement regulation unit is located inside the main body 500 and is formed in a plate shape to be coupled to a lower portion of the diagnostic chip. Upon operation of the diagnostic sample movement regulation unit, the diagnostic chip movement regulation unit is moved by the controller to move the diagnostic chip.

It should be understood that the present invention is not limited thereto and the diagnostic chip movement regulation unit may be configured in any other suitable manner, so long as the diagnostic chip can be transferred by the diagnostic chip movement regulation unit.

Specifically, the diagnostic chip movement regulation unit moves the diagnostic chip upon movement of the diagnostic sample S in the flow channel 12 formed in the diagnostic chip, that is, upon operation of the diagnostic sample movement regulation unit 200, wherein the moving direction of the diagnostic chip is parallel to the moving direction of the diagnostic sample S. Details of operation of the diagnostic chip movement regulation unit upon movement of the diagnostic sample S will be described further below.

The diagnostic sample movement regulation unit 200 regulates movement of the diagnostic sample S by opening/closing the one end of the flow channel 121, that is, the flow channel opening/closing portion, and a method of diagnosing disease from the diagnostic sample S may be varied depending on opening/closing of the flow channel opening/closing portion.

By way of one example, when the diagnostic sample movement regulation unit 200 opens the one end of the flow channel 121, the diagnostic chip movement regulation unit may be operated upon movement of the diagnostic sample S to continuously move the diagnostic chip, wherein the moving direction of the diagnostic chip is opposite the moving direction of the diagnostic sample S.

At the same time, the light source 300 and the sensor 400 may sense the optical information on the diagnostic sample S by continuously illuminating the diagnostic sample S moving through the flow channel.

Here, it is desirable that the movement of the diagnostic sample S precede the movement of the diagnostic chip. This allows sensing of the optical information on the diagnostic sample S to be conducted after the diagnostic sample S sufficiently reacts in the sample buffer unit 122, the pretreatment unit 123, the test unit 124, or the reference unit 125, thereby enabling acquisition of more accurate optical information.

By way of another example, the diagnostic sample movement regulation unit 200 may open/close the one end of the flow channel 121 at a predetermined time interval such that the diagnostic chip movement regulation unit is operated to move/stop the diagnostic chip depending on the position of the diagnostic sample S, wherein the moving direction of the diagnostic chip is opposite the moving direction of the diagnostic sample S.

Here, the light source 300 and the sensor unit 400 may sense the optical information from the diagnostic sample S in a stationary state by illuminating the diagnostic sample S. After completion of the sensing process, the diagnostic sample movement regulation unit 200 may move the diagnostic sample S by opening the flow channel opening/closing portion and, at the same time, the diagnostic chip may be moved.

As described above, depending on the kind of diagnostic sample S and the type of diagnosis, sensing of the optical information on the diagnostic sample S may be performed in an uninterrupted manner without opening and closing the flow channel opening/closing portion, or may be performed in an interrupted manner by temporarily closing the flow channel opening/closing portion through the diagnostic sample movement regulation unit 200 to cease movement of the diagnostic sample S, thereby allowing the optical information on the diagnostic sample S to be measured several times.

Next, movement of the diagnostic sample in the flow channel upon operation of the diagnostic sample movement regulation unit 200 and movement of the diagnostic chip and the optical information detection unit each being operatively associated with the diagnostic sample movement regulation unit upon movement of the diagnostic sample will be described with reference to FIG. 5 and FIG. 6.

Figure 5:
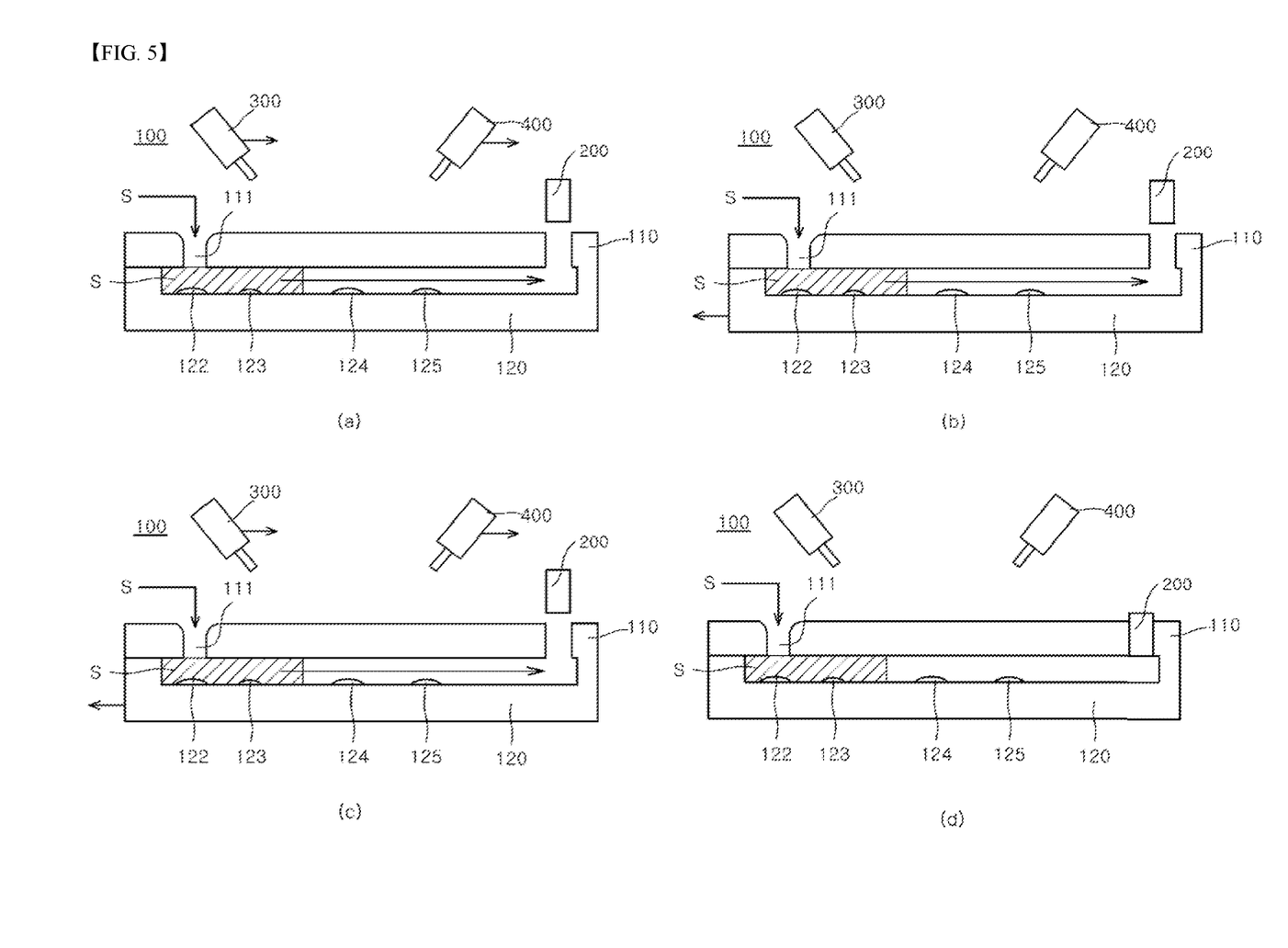
FIG. 5 and FIG. 6 are schematic views showing movement of a diagnostic sample in a flow channel and relative movement between a diagnostic chip and an optical information detection unit upon operation of a diagnostic sample movement regulation unit of the diagnostic kit of FIG. 2.

Referring to FIG. 5(*a*), when the diagnostic sample movement regulation unit 200 opens the flow channel opening/closing portion, the diagnostic sample S moves from the other end of the flow channel to the one end of the flow channel along the flow channel 121.

Upon operation of the diagnostic sample movement regulation unit, movement of the optical information detection unit operatively associated with the diagnostic sample movement regulation unit is controlled, whereby the sensor detects the optical information on the diagnostic sample moving through the flow channel.

That is, the light source 300 and the sensor 400 are moved above the diagnostic sample S at a sensing position to sense the optical information on the diagnostic sample S.

As one alternative, referring to FIG. 5(*b*), when the diagnostic sample movement regulation unit 200 opens the flow channel opening/closing portion, the diagnostic sample S moves from the other end of the flow channel to the one end of the flow channel along the flow channel 121 and the diagnostic chip movement regulation unit is operated to move the diagnostic chip in a direction opposite the moving direction of the diagnostic sample S.

Then, the light source 300 illuminates the diagnostic sample S at a sensing position and the sensor 400 senses the optical information from the diagnostic sample S.

As another alternative, referring to FIG. 5(*c*), when the diagnostic sample movement regulation unit 200 opens the flow channel opening/closing portion, the diagnostic sample S moves from the other end of the flow channel to the one end of the flow channel along the flow channel 121.

Upon operation of the diagnostic sample movement regulation unit 200, the optical information detection unit and the diagnostic chip movement regulation unit are simultaneously operated to control movement of the optical information detection unit and movement of the diagnostic chip, whereby the sensor senses the optical information on the diagnostic sample moving through the flow channel.

Figure 6:
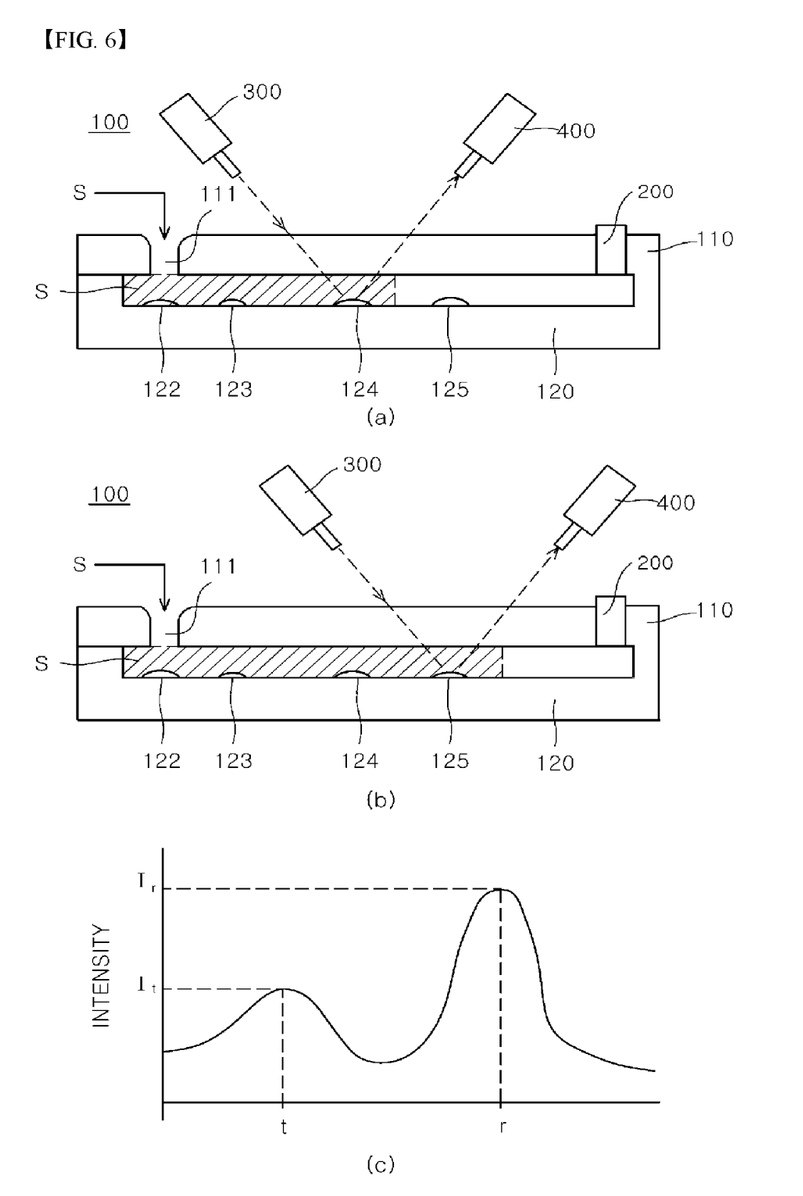

As a further alternative, referring to FIG. 5(*d*) and FIG. 6, when the diagnostic sample movement regulation unit 200 closes the flow channel opening/closing portion, the diagnostic sample S moving along the flow channel 121 is stopped and, at the same time, the diagnostic chip is stopped, whereby the light source 300 illuminates the diagnostic sample S in a stationary state and the sensor 400 senses the optical information on the diagnostic sample S.

Referring to FIG. 6(*a*), through this process, the diagnostic sample S is stopped in the second region, that is, in a region where the test unit 124 is disposed, whereby the light source 300 illuminates the diagnostic sample S and the sensor 400 senses the optical information on the diagnostic sample S, which is defined as value $I_t$ shown in FIG. 6(*c*).

In addition, referring to FIG. 6(*b*), the diagnostic sample S is stopped in the third region, that is, a region where the reference unit 125 is disposed, whereby the light source 300 illuminates the diagnostic sample S and the sensor 400 senses the optical information on the diagnostic sample S, which is defined as value $I_r$ shown in FIG. 6(*c*).

Here, the value $I_t$ is a value defined through a detection material for diagnosing a disease that is to be determined using the diagnostic sample S and the value $I_r$ is a value defined by the reference level of the diagnostic sample S. In FIG. 6, the optical information means intensity of light.

Here, diagnosis of disease through the diagnosis sample S may be conducted based on a value ($I_t/I_r$) obtained by dividing the value $I_t$ by the value $I_r$.

As described above, since the diagnostic chip movement regulation unit and the optical information detection unit are operatively associated with the diagnostic sample movement regulation unit 200 to be controlled by operation of the diagnostic sample movement regulation unit 200, an additional device and process for moving the diagnostic chip and the optical information detection unit can be omitted, thereby allowing easier disease diagnosis.

In addition, since the diagnostic sample S at the same location and under the same conditions can be measured several times through the light source 300 and the sensor 400 by ceasing movement of the diagnostic sample S in the flow channel 121, it is possible to more accurately sense optical information emitted from a target material.

Further, since movement of the diagnostic sample S in the flow channel 121 can be ceased, the diagnostic sample S can be sufficiently pretreated in the pretreatment unit 123.

Moreover, since the controller controls the operation of the diagnostic chip movement regulation unit and the optical information detection unit as well as the operation of the diagnostic sample movement regulation unit 200, not only movement of the diagnostic sample S but also movement of the diagnostic chip and the optical information detection unit can be regulated.

Next, embodiments in which the diagnostic sample movement regulation unit 200 and the diagnostic chip movement regulation unit are operated by the controller of the diagnostic kit according to the present invention will be described with reference to FIG. 8 and FIG. 10.

Figure 8:
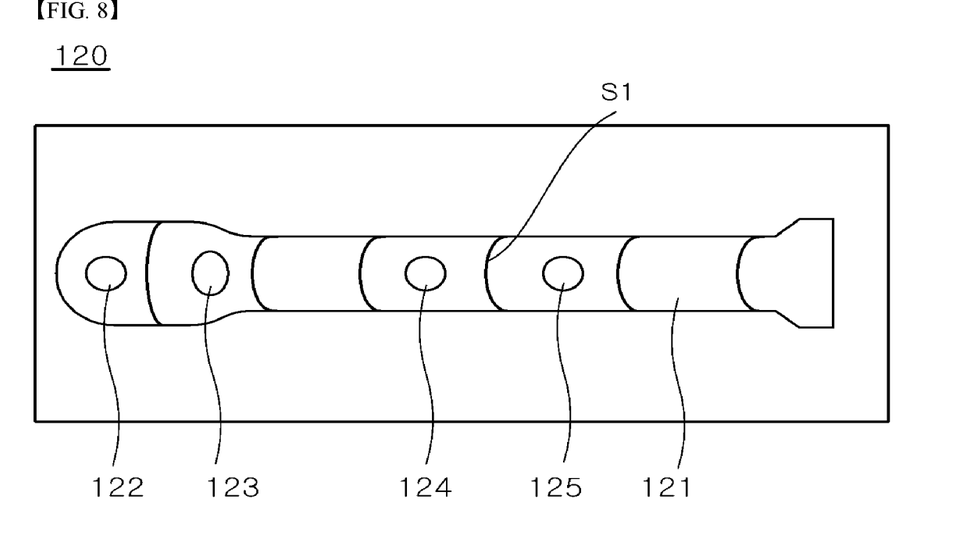
FIG. 8 is a view showing a first embodiment in which a controller of the diagnostic kit according to the present invention controls movement of a diagnostic sample.

In a first embodiment in which movement of the diagnostic sample is controlled by the controller of the diagnostic kit according to the present invention, the controller may regulate movement of the diagnostic sample by controlling the operation of the diagnostic sample movement regulation unit 200 according to a predetermined timing scheme S1, as shown in FIG. 8.

For example, the diagnostic sample movement regulation unit 200 may open/close the flow channel opening/closing portion every one second such that the diagnostic sample S in the flow channel 121 is moved/stopped every one second and, at the same time, the diagnostic chip movement regulation unit moves/stops the diagnostic chip every one second, whereby movement of the diagnostic sample S and the diagnostic chip can be ceased at a time interval of one second to allow sensing of the optical information on the diagnostic sample S.

That is, the diagnostic sample movement regulation unit 200 may open/close the flow channel opening/closing portion at a predetermined time interval to move/stop the diagnostic sample S and the diagnostic chip may be moved/stopped at the predetermined time interval such that the optical information on the diagnostic sample S can be sensed through the light source 300 and the sensor 400 when the diagnostic sample S is in a stationary state, that is, after the diagnostic sample S sufficiently reacts in the sample buffer unit 122, the pretreatment unit 123, the test unit 124, or the reference unit 125, wherein the predetermined time interval may be preset in the controller.

It should be understood that the present invention is not limited thereto and the controller may receive information on the diagnostic sample S to operate/stop the diagnostic sample movement regulation unit 200 and the diagnostic chip movement regulation unit at a predetermined time interval based on the moving speed of the diagnostic sample S, thereby regulating movement of the diagnostic sample S and the diagnostic chip.

That is, data values influencing the moving speed of the diagnostic sample S, such as viscosity and density, or data on the moving speed of the diagnostic sample S may be prestored in the controller such that the controller can regulate movement of the diagnostic sample by controlling the operation of the diagnostic sample movement regulation unit 200 based on the moving speed of the diagnostic sample S.

Figure 9:
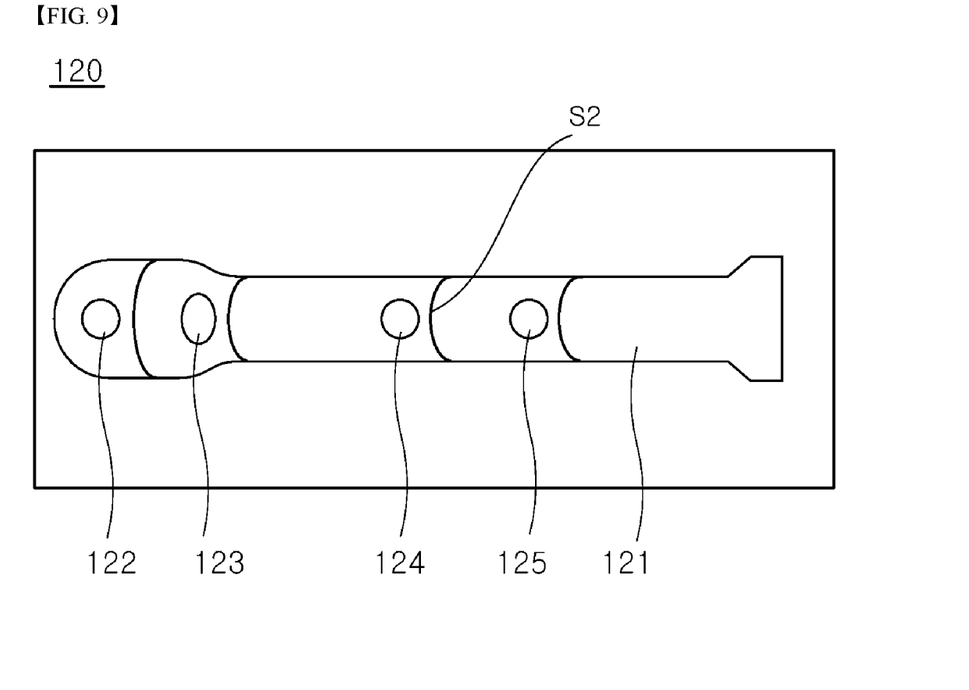
FIG. 9 is a view showing a second embodiment in which a controller of the diagnostic kit according to the present invention controls movement of a diagnostic sample.

In a second embodiment in which movement of the diagnostic sample is controlled by the controller of the diagnostic kit according to the present invention, the controller may control the operation of the diagnostic sample movement regulation unit 200 based on the optical information on the diagnostic sample S acquired by the sensor, as shown in FIG. 9.

That is, progress of the diagnostic sample S in the flow channel 121 may be determined by comparing optical information from the diagnostic sample S passing through the pretreatment unit 123, the test unit 124, or the reference unit 125 with optical information on a normal diagnostic sample S prestored in the controller, whereby the controller can regulate movement of the diagnostic sample S by controlling the operation of the diagnostic sample movement regulation unit 200 based on the determined progress of the diagnostic sample S.

For example, once the sensor 400 senses optical information on the diagnostic sample S passing through the test unit 124, the diagnostic sample movement regulation unit 200 having closed the flow channel opening/closing portion opens the flow channel opening/closing portion to allow the diagnostic sample S to move and the diagnostic chip movement regulation unit moves the diagnostic chip to a position for sensing the next optical information, that is, to a position allowing the light source 300 and the sensor 400 to be located downstream of the reference unit 125, whereby optical information sensing can be performed upon completion of subsequent movement of the diagnostic sample S.

Figure 10:
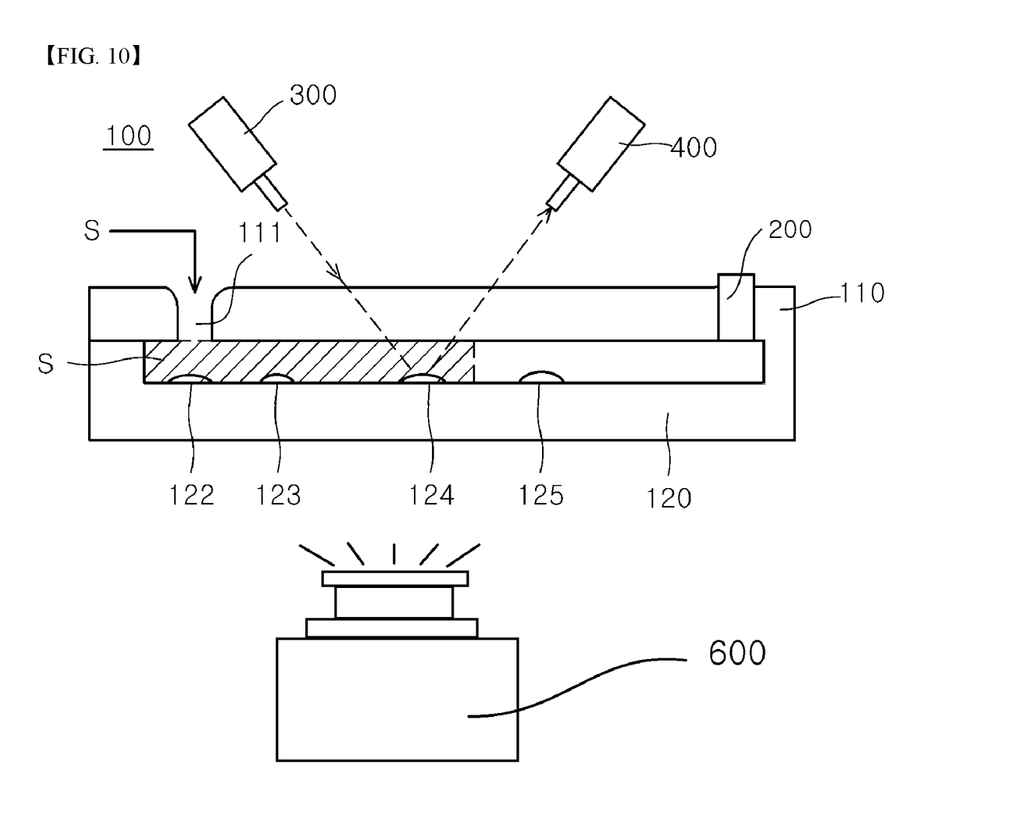
FIG. 10 is a view showing a third embodiment in which a controller of the diagnostic kit according to the present invention controls movement of a diagnostic sample.

In a third embodiment in which movement of the diagnostic sample is controlled by the controller of the diagnostic kit according to the present invention, the controller may regulate movement of the diagnostic sample and the diagnostic chip by controlling the operation of the diagnostic sample movement regulation unit 200 and the diagnostic chip movement regulation unit based on movement of the diagnostic sample S ascertained through the image viewer unit 600, as shown in FIG. 10.

Specifically, the image viewer unit 600 may ascertain movement of the diagnostic sample S through the flow channel 121, whereby the controller can regulate movement of the diagnostic sample S by controlling the operation of the diagnostic sample movement regulation unit 200 based on movement of the diagnostic sample S ascertained by the image viewer unit.

For example, when the image viewer unit 600 ascertains that the diagnostic sample S is passing through the test unit 124, the diagnostic sample movement regulation unit 200 closes the flow channel opening/closing portion for a predetermined period of time such that optical information sensing is sufficiently performed in the test unit and then opens the flow channel opening/closing portion again to resume movement of the diagnostic sample S.

At the same time, the diagnostic chip movement regulation unit moves the diagnostic chip S such that optical information sensing can be performed upon completion of subsequent movement of the diagnostic sample S.

As described above, since the diagnostic sample S in the flow channel 121 can be stopped, sufficient reaction of the diagnostic sample S in the sample buffer unit 122 and the pretreatment unit 123 is possible and the diagnostic sample S under the same conditions can be measured several times through the light source 300 and the sensor 400, thereby enabling more accurate sensing of a target material and optical information from the target material.

It should be understood that the first to third embodiments of the present invention may be applied not only when the diagnostic chip movement regulation unit is controlled upon movement of the diagnostic sample movement regulation unit 200, but also when the optical information detection unit is controlled upon movement of the diagnostic sample movement regulation unit 200 or when the diagnostic chip movement regulation unit and the optical information detection unit are simultaneously controlled upon movement of the diagnostic sample movement regulation unit 200, and detailed description thereof will be omitted.

Next, a modified example of the flow channel of the diagnostic kit according to the present invention will be described with reference to FIG. 7.

Figure 7:
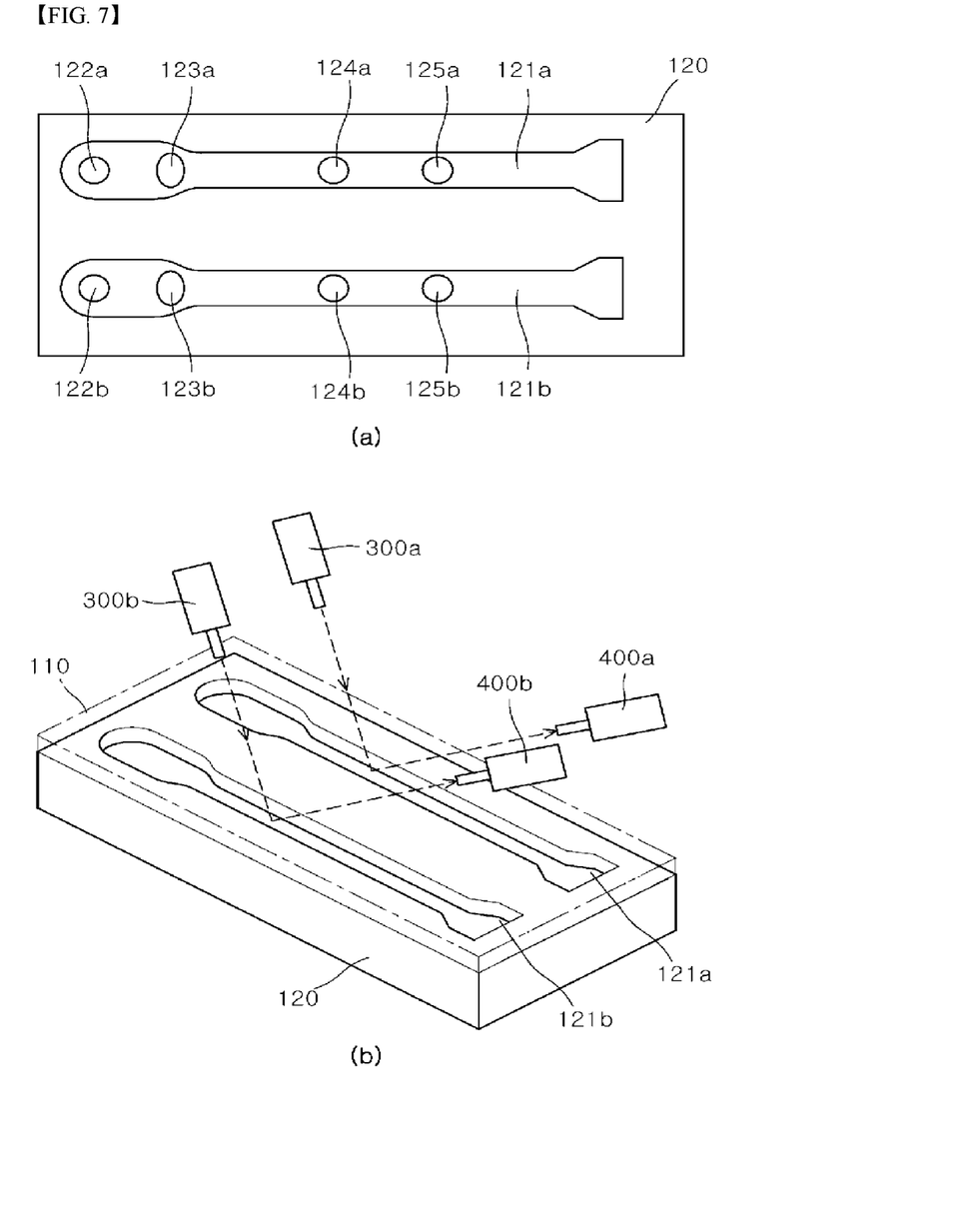
FIG. 7 is schematic view of a modified example of a flow channel of the diagnostic kit according to the present invention.

A flow channel shown in FIG. 7 is formed by the upper plate 110 and the lower plate 120 as in the diagnostic kit according to the above embodiment of the present invention, and detailed description thereof will be omitted.

However, the lower plate 120 includes a first flow channel 121*a* and a second flow channel 121*b* and the upper plate 110 includes a first diagnostic sample input opening (not shown) and a second diagnostic sample input opening (not shown).

Specifically, the first flow channel 121*a* and the second flow channel 121*b* form independent flow paths, respectively, as shown in FIG. 7, and the first diagnostic sample input opening and the second diagnostic sample input opening are connected to the other end of the first flow channel 121*a* and the other end of the second flow channel 121*b*, respectively, such that respective diagnostic samples can be moved into the first flow channel 121*a* and the second flow channel 121*b* through the first diagnostic sample input opening and the second diagnostic sample input opening.

The first flow channel 121*a* is formed with a first sample buffer unit 122*a*, a first pretreatment unit 123*a*, a first test unit 124*a*, and a first reference unit 125*a*. Since these components are the same as those of the diagnostic kit according to the above embodiment, detailed description thereof will be omitted.

In addition, the second flow channel 121*b* has the same configuration as the first flow channel 121*a*, and detailed description thereof will be omitted.

Since the first flow channel 121*a* and the second flow channel 121*b* are independently formed in the lower plate 120 to allow respective diagnostic samples to move therethrough, the diagnostic kit according to this example includes a first light source 300*a* illuminating a diagnostic sample moving through the first flow channel 121*a*, a first sensor 400*a* sensing optical information on the diagnostic sample, a second light source 300*b* illuminating a diagnostic sample moving through the second flow channel 121*b*, and a second sensor 400*b* sensing optical information on the diagnostic sample.

Since the first light source 300*a* and the second light source 300*b* are the same as the light source 300 of the diagnostic kit according to the above embodiment and the first sensor 400*a* and the second sensor 400*b* are the same as the sensor 400 of the diagnostic kit according to the above embodiment, detailed description thereof will be omitted.

Next, a diagnostic kit control method according to the present invention will be described with reference to FIG. 11.

Figure 11:
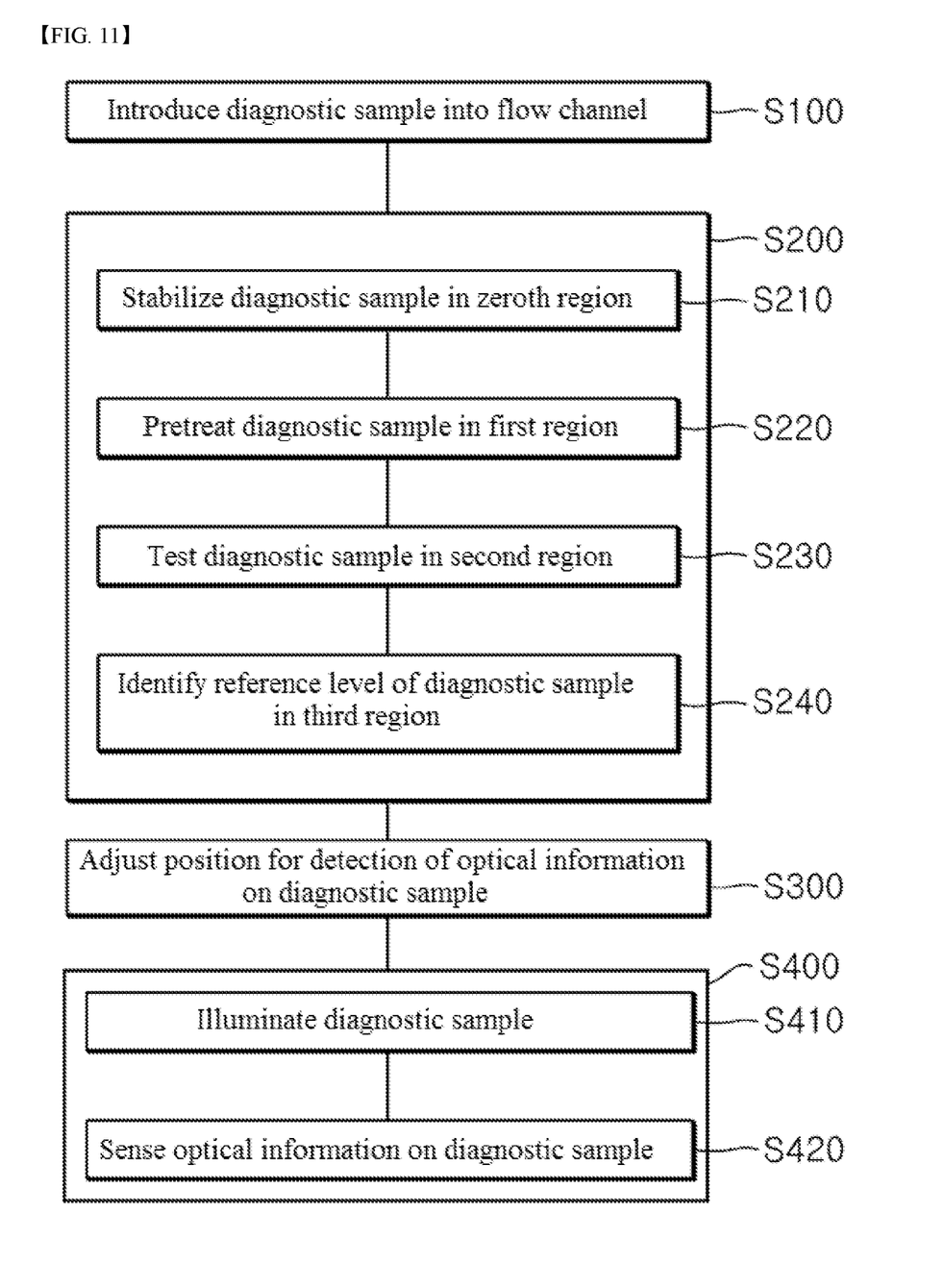
FIG. 11 is a block diagram showing a method of controlling the diagnostic kit according to the present invention.

Referring to FIG. 11, the diagnostic kit control method according to the invention includes a diagnostic sample input step S100, a diagnostic sample moving step S200, a detection position adjustment step S300, and an optical information detection step S400.

In the diagnostic sample input step S100, a diagnostic sample is introduced into the flow channel 121 formed in the diagnostic chip housing through the diagnostic sample input opening 111.

The diagnostic sample moving step S200 is a step of moving the diagnostic sample introduced into the flow channel 121 in the diagnostic sample input step S100. Specifically, the diagnostic sample moving step S200 includes a diagnostic sample buffer step S210, a pretreatment step S220, a test step S230, a reference level identification step S240, and an image viewing step.

In the diagnostic sample buffer step S210, the diagnostic sample is stabilized by the sample buffer unit 122 formed in the zeroth region of the flow channel 121, that is, in a region of the flow channel 121 corresponding to the diagnostic sample input opening 111.

In the pretreatment step S220, the diagnostic sample S is pretreated by the pretreatment unit 123 formed in the first region of the flow channel 121, that is, in a region of the flow channel 121 downstream of the zeroth region in the moving direction of the diagnostic sample S.

In the test step S230, the diagnostic sample S is moved through the test unit 124 formed in the second region of the flow channel 121, that is, in a region of the flow channel 121 downstream of the first region in the moving direction of the diagnostic sample S, such that diagnosis of disease can be conducted based on optical information emitted from the diagnostic sample S upon illuminating the diagnostic sample S.

In the reference level identification step S240, the diagnostic sample S is moved through the reference unit 125 formed in the third region of the flow channel 121, that is, in a region of the flow channel 121 downstream of the second region in the moving direction of the diagnostic sample S, such that the reference level of the diagnostic sample S can be identified based on optical information emitted from the diagnostic sample S upon illuminating the diagnostic sample S.

Here, movement of the diagnostic sample is regulated by the diagnostic sample movement regulation unit 200 opening/closing the one end of the flow channel 121.

In the diagnostic sample moving step, an image of the diagnostic sample moving through the flow channel 121 is viewed through the image viewer unit 600.

In the detection position adjustment step S300, the optical information detection unit and the diagnostic chip are moved relative to each other upon movement of the diagnostic sample S so as to adjust a position for detecting the optical information on the diagnostic sample S.

Specifically, the detection position adjustment step S300 may be performed as follows:

First, in the detection position adjustment step S300, the position for detecting the optical information on the diagnostic sample S may be adjusted by controlling movement of the optical information detection unit upon operation of the diagnostic sample movement regulation unit 200.

Second, the detection position adjustment step S300 may include a diagnostic chip moving step in which the diagnostic chip movement regulation unit 200 moves the diagnostic chip 100. In the detection position adjustment step S300, the diagnostic chip movement regulation unit may be operated upon operation of the diagnostic sample movement regulation unit 200 so as to control movement of the diagnostic chip, thereby adjusting the position for detecting the optical information on the diagnostic sample S.

Third, the detection position adjustment step S300 may include a diagnostic chip moving step in which the diagnostic chip movement regulation unit 200 moves the diagnostic chip 100. In the detection position adjustment step S300, the optical information detection unit and the diagnostic chip movement regulation unit may be simultaneously operated upon operation of the diagnostic sample movement regulation unit 200 so as to control movement of the optical information detection unit and the diagnostic chip, thereby adjusting the position for detecting the optical information on the diagnostic sample S.

In the optical information detection step S400, the optical information detection unit detects the optical information on the diagnostic sample. Specifically, the optical information detection step S400 includes an illumination step S410 and an optical information sensing step S420.

In the illumination step S410, the diagnostic sample S is illuminated, and, in the optical information sensing step S420, the optical information emitted from the diagnostic sample S is sensed. The pretreatment step S220, the test step S230, and the reference level identification step S240 are conducted simultaneously with the illumination step S410 and the optical information sensing step S420.

Since details of the diagnostic kit control method according to the present invention, excluding the diagnostic sample input step S100, the diagnostic sample moving step S200, the detection position adjustment step S300, and the optical information detection step S400, are the same as described relating to the diagnostic kit according to the invention, description thereof will be omitted.

Although some embodiments have been described herein, it should be understood that these embodiments are provided for illustration only and are not to be construed in any way as limiting the present invention, and that various modifications, changes, alterations, and equivalent embodiments can be made by those skilled in the art without departing from the spirit and scope of the invention.

INDUSTRIAL APPLICABILITY

The present invention provides a diagnostic kit used in the healthcare industry, particularly immunochromatographic analysis to determine pregnancy, ovulation, infectious diseases, substance abuse, acute myocardial infarction, cancer and the like. In the diagnostic kit, movement of a diagnostic sample through a flow channel of a diagnostic chip is regulated by a diagnostic sample movement regulation unit while the diagnostic chip is moved by controlling a diagnostic chip movement regulation unit moving the diagnostic chip upon operation of the diagnostic sample movement regulation unit, thereby allowing more accurate diagnosis of disease.

The invention claimed is:

1. A diagnostic kit comprising:
   a diagnostic chip formed with a flow channel through which a diagnostic sample moves;
   a diagnostic sample movement regulation unit opening/closing one end of the flow channel to regulate movement of the diagnostic sample;
   an optical information detection unit detecting optical information on the diagnostic sample; and
   a controller controlling operation of the diagnostic sample movement regulation unit and the optical information detection unit,
   wherein the optical information detection unit comprises:
      a light source illuminating the diagnostic sample; and
      a sensor sensing the optical information emitted from the diagnostic sample,
   the diagnostic sample movement regulation unit is operatively associated with the optical information detection unit, and
   the diagnostic chip and the optical information detection unit are moved relative to each other upon operation of the diagnostic sample movement regulation unit, whereby the optical information detection unit detects the optical information on the diagnostic sample moving through the flow channel,
   wherein the diagnostic chip comprises:
      a diagnostic chip housing comprising an upper plate and a lower plate and formed therein with the flow channel;
      a diagnostic sample input opening formed on the upper plate and connected to the other end of the flow channel to allow the diagnostic sample to be introduced therethrough;
      a pretreatment unit disposed in a first region of the flow channel and provided with a material for pretreatment of the diagnostic sample moved from the diagnostic sample input opening;
      a test unit disposed in a second region of the flow channel and provided with a material for testing of the diagnostic sample moved from the first region; and
      a reference unit disposed in a third region of the flow channel and provided with a reference material of the diagnostic sample moved from the second region.

2. The diagnostic kit according to claim 1, wherein, the optical information detection unit is moved by the controller to be moved relative to the diagnostic chip upon operation of the diagnostic sample movement regulation unit.

3. The diagnostic kit according to claim 1, further comprising:
   a diagnostic chip movement regulation unit moving the diagnostic chip,
   wherein relative movement between the diagnostic chip and the optical information detection unit is achieved through operative association between the diagnostic chip movement regulation unit and the diagnostic sample movement regulation unit.

4. The diagnostic kit according to claim 3, wherein, upon operation of the diagnostic sample movement regulation unit, the diagnostic chip movement regulation unit is operated by the controller to move the diagnostic chip such that the diagnostic chip and the optical information detection unit are moved relative to each other.

5. The diagnostic kit according to claim 3, wherein, upon operation of the diagnostic sample movement regulation unit, the optical information detection unit and the diagnostic chip movement regulation unit are simultaneously operated by the controller to control movement of the diagnostic chip and the optical information detection unit such that the diagnostic chip and the optical information detection unit are moved relative to each other.

6. The diagnostic kit according to claim 3, wherein sensing of the optical information on the diagnostic sample is performed such that the diagnostic sample movement regulation unit opens the one end of the flow channel to move the diagnostic sample such that at least one of the diagnostic chip movement regulation unit and the optical information detection unit is operated to move at least one of the diagnostic chip and the optical information detection unit, while the light source and the sensor sense the optical information on the diagnostic sample by illuminating the diagnostic sample, or such that the diagnostic sample movement regulation unit opens/closes the one end of the flow channel at a predetermined time interval such that at least one of the diagnostic chip movement regulation unit and the optical information detection unit is operated to move/stop at least one of the diagnostic chip and the optical information detection unit depending on position of the diagnostic sample, and the light source and the sensor sense the optical information on the diagnostic sample by illuminating the diagnostic sample when the diagnostic sample and the diagnostic chip are in a stationary state.

7. The diagnostic kit according to claim 3, wherein the controller regulates movement of the diagnostic sample by controlling operation of the diagnostic sample movement regulation unit according to a predetermined timing scheme.

8. The diagnostic kit according to claim 7, wherein data on a moving speed of the diagnostic sample is prestored in the controller and the controller regulates movement of the diagnostic sample and the diagnostic chip by controlling operation of the diagnostic sample movement regulation unit and operation of at least one of the diagnostic chip movement regulation unit and the optical information detection unit according to a predetermined timing scheme based on the data on the moving speed of the diagnostic sample.

9. The diagnostic kit according to claim 7, wherein the controller regulates movement of the diagnostic sample and the diagnostic chip by controlling operation of the diagnostic sample movement regulation unit and operation of at least one of the diagnostic chip movement regulation unit and the optical information detection unit based on the optical information on the diagnostic sample acquired by the sensor.

10. The diagnostic kit according to claim 7, further comprising:
an image viewer unit showing a moving image of the diagnostic sample,
wherein the controller regulates movement of the diagnostic sample and the diagnostic chip by controlling operation of the diagnostic sample movement regulation unit and operation of at least one of the diagnostic chip movement regulation unit and the optical information detection unit based on movement of the diagnostic sample ascertained through the image viewer unit.

11. A method of controlling a diagnostic kit, comprising:
a diagnostic sample input step in which a diagnostic sample is introduced into a flow channel formed in a diagnostic chip through a diagnostic sample input opening;
a diagnostic sample moving step in which the diagnostic sample is moved along the flow channel;
a detection position adjustment step in which, upon movement of the diagnostic sample, the diagnostic chip and an optical information detection unit detecting optical information on the diagnostic sample are moved relative to each other to adjust a position for detecting the optical information on the diagnostic sample; and
an optical information detection step in which the optical information detection unit detects the optical information on the diagnostic sample, the optical information detection step comprising: an illumination step in which a light source illuminates the diagnostic sample; and an optical information sensing step in which a sensor senses the optical information emitted from the diagnostic sample,
wherein the diagnostic sample moving step and the detection position adjustment step are conducted by a controller,
movement of the diagnostic sample in the diagnostic sample moving step is regulated by a diagnostic sample movement regulation unit opening/closing one end of the flow channel and,
in the detection position adjustment step, the optical information detection unit is operatively associated with the diagnostic sample movement regulation unit to be controlled by operation of the diagnostic sample movement regulation unit,
wherein the diagnostic sample moving step comprises:
a pretreatment step in which the diagnostic sample moved from the diagnostic sample input opening is pretreated in a first region;
a test step in which the diagnostic sample moved from the first region is tested in a second region; and
a reference level identification step in which a reference level of the diagnostic sample moved from the second region is identified in a third region.

12. The method according to claim 11, wherein, in the detection position adjustment step, the optical information detection unit is moved by the controller to be moved relative to the diagnostic chip upon operation of the diagnostic sample movement regulation unit.

13. The method according to claim 11, wherein the detection position adjustment step comprises a diagnostic chip moving step in which the diagnostic chip is moved by a diagnostic chip movement regulation unit and the relative movement between the diagnostic chip and the optical information detection unit in the detection position adjustment step is achieved through operative association between the diagnostic chip movement regulation unit and the diagnostic sample movement regulation unit.

14. The method according to claim 13, wherein, in the detection position adjustment step, the diagnostic chip movement regulation unit is operated by the controller upon operation of the diagnostic sample movement regulation unit to move the diagnostic chip such that diagnostic chip and the optical information detection unit are moved relative to each other.

15. The method according to claim 13, wherein, in the detection position adjustment step, the optical information detection unit and the diagnostic chip movement regulation unit are simultaneously operated by the controller upon operation of the diagnostic sample movement regulation unit so as to control movement of the diagnostic chip and the optical information detection unit such that the diagnostic chip and the optical information detection unit are moved relative to each other.

16. The method according to claim 13, wherein sensing of the optical information on the diagnostic sample is performed such that, in the diagnostic sample moving step, the diagnostic sample movement regulation unit opens the one end of the flow channel to move the diagnostic sample such that at least one of the diagnostic chip movement regulation unit and the optical information detection unit is operated to move at least one of the diagnostic chip and the optical information detection unit in the detection position adjustment step, while the light source and the sensor sense the optical information on the diagnostic sample by illuminating the diagnostic sample, or such that, in the diagnostic sample moving step, the diagnostic sample movement regulation unit opens/closes the one end of the flow channel at a predetermined time interval such that at least one of the diagnostic chip movement regulation unit and the optical information detection unit is operated to move/stop at least one of the diagnostic chip and the optical information detection unit depending on position of the diagnostic sample in the detection position adjustment step, and the light source and the sensor sense the optical information on the diagnostic sample by illuminating the diagnostic sample when the diagnostic sample and the diagnostic chip are in a stationary state.

17. The method according to claim 13, wherein, in the diagnostic sample moving step, the controller regulates movement of the diagnostic sample by controlling operation of the diagnostic sample movement regulation unit according to a predetermined timing scheme.

18. The method according to claim 17, wherein, in the diagnostic sample moving step, the controller operates the diagnostic sample movement regulation unit based on data on a moving speed of the diagnostic sample, the data being prestored in the controller, and, in the detection position adjustment step, the controller regulates movement of the diagnostic sample and the diagnostic chip by controlling operation of at least one of the diagnostic chip movement regulation unit and the optical information detection unit according to a predetermined timing scheme.

19. The method according to claim 17, wherein, in the diagnostic sample moving step, the controller operates the diagnostic sample movement regulation unit based on the optical information on the diagnostic sample acquired by the sensor, and, in the detection position adjustment step, the controller regulates movement of the diagnostic sample and the diagnostic chip by controlling operation of at least one of the diagnostic chip movement regulation unit and the optical information detection unit.

20. The method according to claim 17,
wherein the diagnostic sample moving step comprises an image viewing step in which a moving image of the diagnostic sample moving though the flow channel is viewed through an image viewer unit, and
wherein the controller operates the diagnostic sample movement regulation unit based on movement of the diagnostic sample ascertained through the image viewer unit in the diagnostic sample moving step and regulates movement of the diagnostic sample and the diagnostic chip in the detection position adjustment step by controlling operation of at least one of the diagnostic chip movement regulation unit and the optical information detection unit.

* * * * *